(12) United States Patent
Kumasaka

(10) Patent No.: US 6,451,001 B2
(45) Date of Patent: *Sep. 17, 2002

(54) DISPOSABLE ABSORBENT ARTICLE

(75) Inventor: Yoshinori Kumasaka, Kagawa-ken (JP)

(73) Assignee: Uni-Charm Corporation, Ehime-ken (JP)

(*) Notice: Subject to any disclaimer, the term of this patent is extended or adjusted under 35 U.S.C. 154(b) by 0 days.

This patent is subject to a terminal disclaimer.

(21) Appl. No.: 09/903,479

(22) Filed: Jul. 11, 2001

Related U.S. Application Data

(62) Division of application No. 09/160,599, filed on Sep. 25, 1998, now Pat. No. 6,293,934.

(30) Foreign Application Priority Data

Sep. 30, 1997 (JP) ............................................. 9-267415

(51) Int. Cl.⁷ ................................................. A61F 13/15
(52) U.S. Cl. ............................ 604/385.27; 604/385.28; 604/385.3
(58) Field of Search ................. 604/378, 385.24–385.3, 604/386, 387, 392–402

(56) References Cited

U.S. PATENT DOCUMENTS

| | | | |
|---|---|---|---|
| 5,304,159 A | | 4/1994 | Tanji et al. |
| 5,904,674 A | | 5/1999 | Bonjour |
| 6,186,996 B1 | * | 2/2001 | Martin |
| 6,293,934 B1 | * | 9/2001 | Kumasaka ............. 604/385.27 |

FOREIGN PATENT DOCUMENTS

| | | |
|---|---|---|
| GB | 2 280 095 | 1/1995 |
| JP | 2-71521 | 5/1990 |
| JP | 2-152450 | 6/1990 |
| JP | 4-90322 | 8/1992 |
| JP | 8-215239 | 8/1996 |
| WO | 95/02381 | 1/1995 |
| WO | 96/22755 | 8/1996 |

* cited by examiner

Primary Examiner—Aaron J. Lewis
Assistant Examiner—K. M. Reichle
(74) Attorney, Agent, or Firm—Baker & Daniels

(57) ABSTRACT

An absorbent article having a pair of side flaps along transversely opposite side edges of the article. Each of the side flaps is formed on its upper surface with a plurality of pleats that extend longitudinally of the side flap. Each of the pleats contains an elastically stretchable/contractile member that extends along its distal edge so as to operate longitudinally of the pleat.

13 Claims, 2 Drawing Sheets

DISPOSABLE ABSORBENT ARTICLE

RELATED APPLICATIONS

This is a Divisional of U.S. patent application Ser. No. 09/160,599, filed on Sep. 25, 1998 now U.S. Pat. No. 6,293,934.

BACKGROUND OF THE INVENTION

This invention relates to disposable absorbent articles and more particularly to such articles as disposable diapers, sanitary napkins or the like that are used for absorption and containment of body exudates.

Absorbent articles of such type are well known and generally comprises a liquid-permeable topsheet, a liquid-impermeable backsheet, a liquid-absorbent core disposed between these two sheets and a pair of elastically stretchable/contractile side flaps being contiguous to and extending along transversely opposite side edges of the core. Disposable diapers are also well known which include paired side flaps that comprise a first pair of elastically stretchable/contractile side flaps that extend outward from transversely opposite side edges of a liquid-absorbent cores and a second pair of elastically stretchable/contractile side flaps that are contiguous to and extend along transversely opposite side edges of the core.

Japanese Patent Application Disclosure (Kokai) No. Hei8-215239 discloses a disposable diaper having first and second pairs of side flaps, each of the second side flaps being folded in a zigzag manner to form a plurality of pleats between its proximal edge and its distal edge. These pleats contain elastically stretchable/contractile members extending along their apices, respectively.

In the case of the well known disposable diaper disclosed in Japanese Patent Application Disclosure (Kokai) No. Hei8-215239, the second pair of side flaps have pleats that are adapted to come elastically into line-contact with the wearer's skin along the apices of the respective pleats. However, a region defined between the apex of the outermost pleat and the distal edge of the second side flap often comes elastically into surface-contact with the wearer's skin. Such surface-contact is certainly effective to prevent leakage of body exudates but may cause skin eruption over a large area. In addition, the pleats are relatively large and the sheet material for the second side flaps must be relatively large. Consequently, the manufacturing cost of diaper is correspondingly increased.

SUMMARY OF THE INVENTION

In view of the above problems, the invention provides a disposable absorbent article such as a disposable diaper having paired side flaps adapted to come into line-contact with the wearer's skin along a plurality of lines preferably under an elastic effect. This configuration is able to more effectively protect the wearer's skin from eruption than side flaps that cause surface-contact.

According to one aspect of the invention, there is provided a disposable absorbent article having a symmetric shape with respect to a longitudinal center line thereof and comprises a liquid-permeable topsheet, a liquid-impermeable backsheet, a liquid-absorbent core disposed therebetween. The absorbent article further comprises elastically stretchable/contractile side flaps that are continuous to and extend along transversely opposite side edges of the core. The side flaps respectively have first proximal edges, first distal edges, upper surfaces intended to come in contact with the wearer's skin and lower surfaces intended not to come in contact with the wearer's skin. The side flaps are formed on their upper surfaces with a plurality of pleats extending longitudinally of the side flaps. The pleats are spaced one from another between the first proximal edges and the first distal edges. The pleats respectively have second proximal edges on the upper surfaces which serve as their bases and second distal edges that are normally biased to rise up toward the wearer's skin.

According to another aspect of the invention, there is provided disposable absorbent article having a symmetric shape with respect to a longitudinal center line thereof and comprising a liquid-permeable topsheet, a liquid-impermeable backsheet, a liquid-absorbent core disposed therebetween. This absorbent article further comprises a pair of elastically stretchable/contractile side flaps that extend outward from transversely opposite side edges of the core. Each of the side flaps has a first proximal edge, a first distal edge, an upper surface intended to come in contact with the wearer's skin, and a lower surface intended not to come in contact with the wearer's skin. Each of the side flaps is formed on their upper surfaces with plural pleats that extend longitudinally of the side flaps. The pleats are spaced one from another between the first proximal edge and the first distal edge. Each of the pleats has a second proximal edge on the upper surface of the side flap which serve as a base thereof and a second distal edge that is normally biased to rise up toward the wearer's skin.

DESCRIPTION OF THE PREFERRED EMBODIMENTS

Details of a disposable absorbent article according to the invention will be more fully understood from the description of a disposable diaper provided as a specific embodiment of the invention given hereunder with reference to the accompanying drawings.

Figure 1:
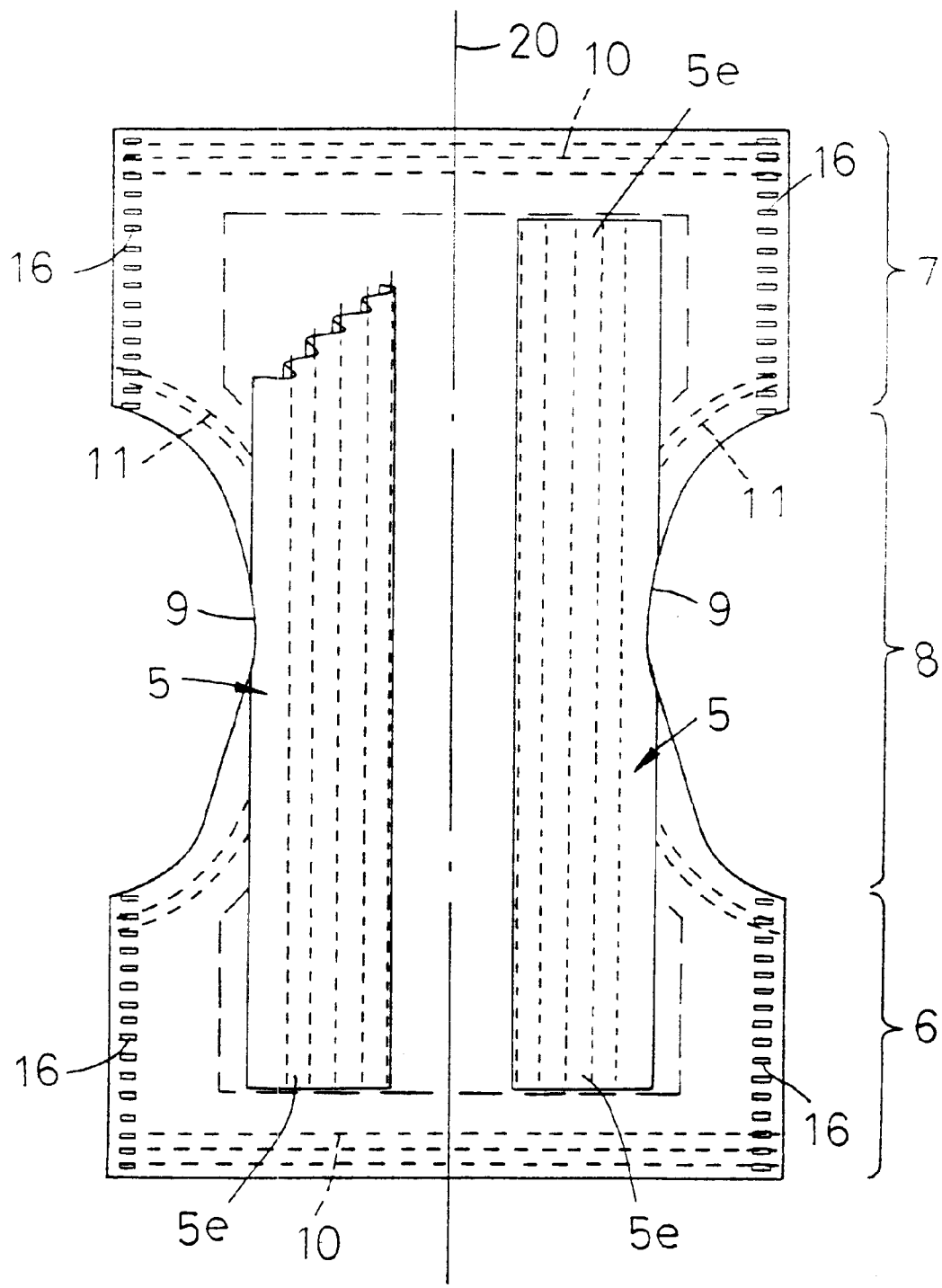
FIG. 1 is a plan view depicting a partly cutaway disposable absorbent article according to the invention implemented in the form of disposable diaper.
Figure 2:
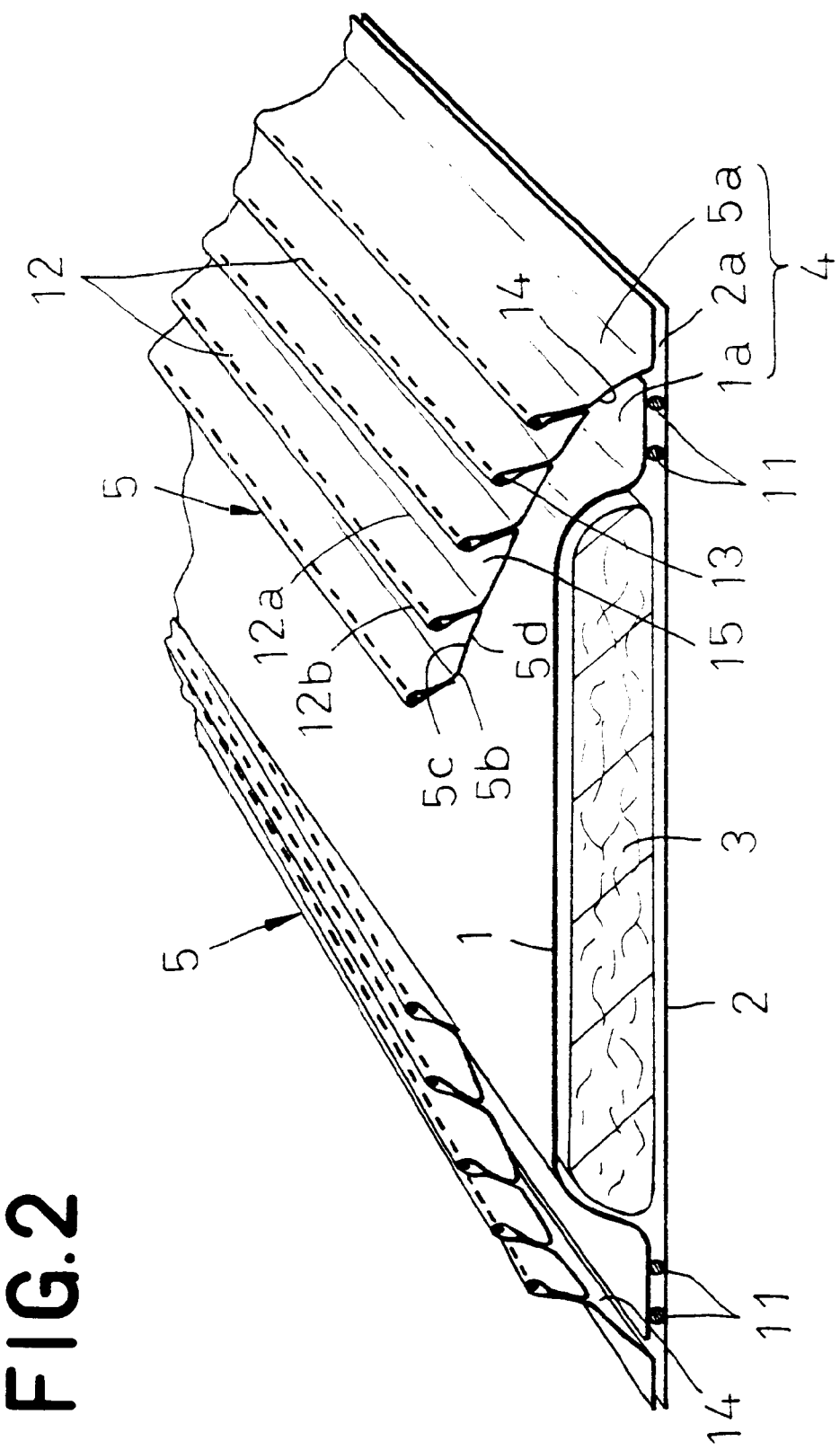
FIG. 2 is a perspective view schematically depicting the diaper in a transverse sectional view.

Referring to FIGS. 1 and 2, an article comprises a liquid-permeable topsheet 1, a liquid-impermeable backsheet 2, a semi-rigid hourglass-shaped liquid-absorbent core 3 disposed between these two sheets 1, 2, a first pair of side flaps 4 each having a high flexibility, and a second pair of side flaps 5 each having a high flexibility and extending between a first proximal edge 5a and a second distal edge 5b. The article is symmetric with respect to a longitudinal center line 20 and includes front and rear waist regions 6, 7 and a crotch region 8. Each of the first side flaps 4 comprises respective portions 1a, 2a of the topsheet 1 and the backsheet 2 that extends outward beyond the associated side edge of the core 3 and a proximal edge 5a of the associated second side flap 5 that is bonded to the outermost edge of the portion 2a. Portions of the topsheet 1 and the backsheet 2 extending outward beyond peripheral edges of the core 3 are bonded together by means of hot melt adhesive or heat-sealing means (not shown) and define along their transversely opposite side edges a pair of inwardly curved edges 9 intended to surround of the wearer's legs. Portions of the topsheet 1 and the backsheet 2 extending outward beyond longitudinally opposite ends of the core 3 contain therebetween elastically stretchable/contractile members 10 which extend transversely of the waist regions 7. Portions of the topsheet 1 and the backsheet 2 extending outward beyond transversely opposite side edges of the core 3 contain therebetween elastically stretchable/contractile members 11 which extend along the inwardly curved edges 9. These elastically stretchable/contractile members 10, 11 are secured under appropriate tensions to the foresaid portions by means of hot melt adhesive (not shown).

Each of the second side flaps 5 has an upper surface 5c intended to face the wearer's skin and a lower surface 5d intended not to come into contact with the wearer's skin. On the upper surface 5c of the second flap 5, a plurality of pleats 12 are formed which extend longitudinally of the second side flap 5 and are spaced one from another. Each of these pleats 12 has a second proximal edge 12a having the upper surface 5c as its base with the other pleats 12 and a second distal edge 12b normally biased to rise up toward the wearer's skin. The second distal edges 12b of the respective pleats 12 contain elastically stretchable/contractile members 13 extending therein longitudinally of these second distal edges 12b and are secured thereto under appropriate tension by means of hot melt adhesive (not shown). While the respective members 13 may have substantially the same stretch stress, it is also possible to configure members 13 so that their stretch stress gradually increases or decreases from the first distal edge 5b to the first proximal edge 5a of the second side flap 5 or so that the stretch stress in the vicinity of the first distal edge 5b is higher or lower than the stretch stress in the vicinity of the first proximal edge 5a. The respective pleats 12 have substantially the same height as measured from their second proximal edges 12a to their second distal edges 12b and a distance between each pair of adjacent second proximal edges 12a is preferably dimensioned to be larger than the height in order to ensure that the respective distal edges 12b should not overlap one another when the respective pleats 12 are collapsed. The height is preferably 2~15 mm. While the proximal edges 12a of the respective pleats 12 are illustrated as being in closed state, they may also be in opened state. The respective second side flaps 5 are oriented from the first proximal edges 5a toward the longitudinal center line 20 with their first distal edges 5b lying more close to the longitudinal center line 20 than the first proximal edges 5a. Each of the second side flaps 5 is bonded at longitudinally opposite ends 5e thereof to an upper surface of the topsheet 1 by means of hot melt adhesive or heat-sealing (not shown) with the first distal edge 5b lying on the upper surface of the topsheet 1 in its region overlying the core 3. With such arrangement, first channels 14 adapted to receive body exudates are defined between lower surfaces 5d of the respective second side flaps 5 and the topsheet 1. It is also possible to orient the respective second side flaps 5 inversely with respect to the aforesaid orientation, i.e., outwardly of the diaper. In this case, the lower surfaces 5d of the respective second side flaps 5 will face the wearer's skin and the respective pleats 12 will be formed on this surface 5d. The respective pleats 12 will be oriented toward the longitudinal center line 20 so that the second distal edges 12b are more adjacent to the longitudinal center line 20 than the second proximal edges 12a. With such arrangement, second channels 15 adapted to receive body exudates are defined between the upper surfaces 5c and each of pleats 12 although these second channels 15 are smaller than the first channels 14.

Even if body exudates discharged on the upper surface of the topsheet 1 between the second pair of side flaps 5 flows laterally, such body exudates are first prevented by the second pair of side flaps 5 from further flowing sideways. Should body exudates overcome such blocking effect and flow onto the upper surfaces of the second pair of side flaps 5, such body exudates will be blocked by the plural pleats 12 in a multi-stage mode. Accordingly, there is practically no apprehension that body exudates might overflow the second pair of side flaps 5 to the first pair of side flaps 4. Even if a flow of body exudates reach the first pair of side flaps 4 (though there is substantially no possibility), body exudates will be eventually prevented by these first side flaps 4 from leaking outward. As is apparent, it is preferable, but not essential, to provide the first pair of side flaps 4.

While the figures depict an open type diaper in the transversely opposite side edges 16 of the front and rear waist regions are not bonded together, the invention is applicable also to the diaper of shorts or pull-on type in which the side edges are bonded together.

Components of the diaper may be made of materials conventionally employed for components of the disposable absorbent articles such as diapers and sanitary napkins. For example, a hydrophobic or hydrophilic fibrous nonwoven fabric may be employed as material of the topsheet 1 and a moisture-permeable plastic film or such plastic film having its outer surface laminated with a hydrophobic fibrous nonwoven fabric may be employed as material of the backsheet 2. A mixture of fluff pulp and polymer particles of high water absorptivity appropriately compressed may be employed as material for the core 3. The second pair of side flaps 5 may be made of a hydrophobic fibrous nonwoven fabric. The second pair of side flaps 5 are preferably water repellent finished by well known process that give them a desired waterproof characteristic. As will be understood from the foregoing description, the first pair of side flaps 4 are liquid-impermeable and the second pair of side flaps 5 are liquid-resistant. The term "liquid-resistant" used herein should be understood to mean that these side flaps 5 are liquid-permeable under a predetermined or higher pressure but substantially impervious or hardly pervious to body exudates such as urine so long as the diaper is normally worn. The first pair of side flaps 4 may be formed from sheet material other than the topsheet 1 and the backsheet 2 and are bonded to the transversely opposite side edges of the core 3 so far as such sheet material is liquid-impermeable.

The disposable absorbent article according to the invention includes the side flaps formed with a plurality of pleats adapted to come into line-contact with the wearer's skin along the lines defined by the plurality of pleats preferably under an elastic effect. Therefore, the side flaps according to the invention can prevent leakage of body exudates as effectively as or more effectively than the diaper having the side flaps of surface contact type and can avoid eruption from possibly appearing on the wearer's skin more effectively than the side flaps of surface contact type.

The side flaps according to the invention have the plural pleats of which the height may be relatively small and can be formed from correspondingly narrow sheet material. Consequently, an increase in manufacturing cost of the article due to formation of the pleats can be alleviated.

What is claimed is:

1. A disposable absorbent article having a symmetric shape with respect to a longitudinal center line thereof, comprising:
    a liquid-permeable topsheet;
    a liquid-impermeable backsheet;
    a liquid-absorbent core disposed therebetween; and
    elastically stretchable/contractile side flaps being contiguous to and extending along transversely opposite side edges of said core, wherein:

each of said side flaps has a first proximal edge, a first distal edge, an upper surface for contacting a wearer's skin and an opposite lower surface, each of said side flaps having a plurality of pleats formed on its upper surface, said plurality of pleats extending longitudinally of the associated one of said side flaps and spaced one from another between said first proximal edge and said first distal edge; and each of said plurality of pleats has a second proximal edge located at said upper surface of the associated one of said flaps and a second distal edge normally biased to rise up above said upper surface of the associated one of said flaps in a direction adapted to be toward the wearer's skin, said upper surface of each of said side flaps defining a common base to which the second proximal edge of each associated pleat is secured spaced from the other proximal edges associated with said side flap.

2. The article according to claim 1, wherein each of said pleats has an elastically stretchable/contractile member along its second distal edge.

3. The article according to claim 1, wherein each of said pleats is substantially similar in height as measured from said second proximal edge to said second distal edges and are spaced apart from one another by a distance which is larger than said similar height.

4. The article according to claim 1, wherein the first distal edge of each of said side flaps lies closer to said longitudinal center line than to the associated one of said proximal edges.

5. The article according to claim 1, wherein a first channel is defined between said lower surface of each of said side flaps and said topsheet.

6. The article according to claim 5, wherein second channels smaller than said first channels are defined between said upper surface of each of said side flaps and said respective pleats.

7. The article according to claim 1, wherein said side flaps are moisture-permeable and liquid-resistant.

8. The article according to claim 1, wherein each of said plurality of pleats is formed from a single layer of material which is folded along the associated second distal edge to define opposite sides which extend between the associated second proximal edge and second distal edge.

9. A disposable absorbent article having a symmetric shape with respect to a longitudinal center line thereof comprising:

a liquid-permeable topsheet;

a liquid-impermeable backsheet;

a liquid-absorbent core disposed therebetween;

a first pair of elastically stretchable/contractile side flaps extending outward from transversely opposite side edges of said core; and a second pair of elastically stretchable/contractile side flaps being contiguous to and extending along said transversely opposite side edges of said core, wherein:

each of said second pair of side flaps has a first proximal edge, a first distal edge, an upper surface for contacting a wearer's skin and an opposite surface, each of said second pair of side flaps having a plurality of pleats formed on its upper surface, said plurality of pleats extending longitudinally of the associated one of said side flaps and spaced from one another between said first proximal edge and said first distal edge; and each of said plurality of pleats has a second proximal edge located at said upper surface of the associated one of said flaps and a second distal edge normally biased to rise up above said upper surface on the associated one of said flaps in a direction adapted to be toward the wearer's skin, said upper surface of each of said side flaps defining a common base to which the second proximal edge of each associated pleat is secured spaced from the other proximal edges associated with said side flap.

10. The article according to claim 9, wherein each of said pleats has an elastically stretchable/contractile member along its second distal edge.

11. The article according to claim 9, wherein each of said pleats is substantially similar in height as measured from said second proximal edges to said second distal edges and are spaced apart from one another by a distance which is larger than said similar height.

12. The article according to claim 9, wherein the first distal edge of each of said side flaps lies closer to said longitudinal center line than to the associated one of said first proximal edges.

13. The article according to claim 9 wherein each of said plurality of pleats is formed from a single layer of material which is folded along the associated distal edge to define opposite sides which extend between the associated base and distal edge.

* * * * *